United States Patent [19]

Oediger et al.

[11] 4,209,445
[45] Jun. 24, 1980

[54] PROCESS FOR THE PREPARATION OF PIPERONYLIDENECROTONIC ACID AMIDES

[75] Inventors: Hermann Oediger; Andreas Schulze, both of Cologne, Fed. Rep. of Germany

[73] Assignee: Haarman & Reimer GmbH, Holzminden, Fed. Rep. of Germany

[21] Appl. No.: 969,113

[22] Filed: Dec. 13, 1978

[30] Foreign Application Priority Data

Dec. 22, 1977 [DE] Fed. Rep. of Germany ....... 2757483

[51] Int. Cl.² ............................................. C07D 317/44
[52] U.S. Cl. ......................... 260/340.5 R; 260/239 B; 260/326.4; 544/109; 546/245
[58] Field of Search ..................... 260/340.5 R, 559 R

[56] References Cited

U.S. PATENT DOCUMENTS

| | | | |
|---|---|---|---|
| 2,951,853 | 9/1960 | Matsui et al. .................. | 260/347.5 |
| 4,021,574 | 5/1977 | Bollag et al. .................. | 260/559 R |

*Primary Examiner*—Ethel G. Love
*Attorney, Agent, or Firm*—Sprung, Felfe, Horn, Lynch & Kramer

[57] ABSTRACT

Process for the preparation of piperonylidenecrotonic acids amides of the formula

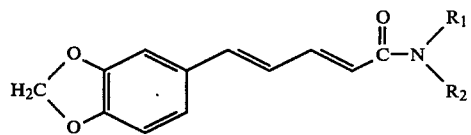

in which
$R_1$ and $R_2$ have the meaning given in the disclosure wherein piperonal is reacted with crotonic acid amides of the formula

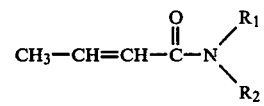

in the presence of hydroxides of the formula

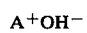

in which
A+ represents a quaternary ammonium or phosphonium group or an alkali metal complex with neutral organic complex ligands, and polar aprotic or polar, sterically hindered protic organic solvents which are inert under the reaction conditions.

6 Claims, No Drawings

PROCESS FOR THE PREPARATION OF PIPERONYLIDENECROTONIC ACID AMIDES

The present invention relates to a new process for the preparation of piperonylidenecrotonic acid amides.

Piperonylidenecrotonic acid amides have diverse industrial uses. Thus, piperonylidenecrotonic acid piperidide (trivial name: piperine) is an important aromatic essence. It is the hot ingredient of black pepper (Chromatographia Volume 8 (1975), pages 342–344). Further suitable aromatic essences for rounding off the flavour of pepper formulations are piperonylidenecrotonic acid pyrrolidide, also called piperyline (Chem. Ber. Volume 103 (1970), pages 3,752–3,770) and piperonylidenecrotonic acid isobutylamide, also called piperlonguminine (Tetrahedron Volume 23 (1967), pages 1,769–1,781). Piperine is also used as an additive to germicidal formulations (U.S. Pat. No. 2,085,064). Piperonylidenecrotonic acid amides are also suitable as insecticides or synergistic agents for insecticides (U.S. Pat. No. 2,487,179; Contrib. Boyce Thompson Inst. Volume 13 (1945) pages 433–442; Russian Pat. No. 222,056; and DT-OS (German Published Specification) 2,413,756). Furthermore, piperine is also suitable as an analeptic agent in cases of morphine or barbiturate poisoning (J. Res. Indian Med. Volume 8 (1973), pages 1–9 and Volume 9 (1974) pages 17–22).

Various processes have therefore already been proposed for the preparation of piperonylidenecrotonic acid amides, in particular of piperine. Thus, according to one preparation process, piperonal is first converted into piperonylideneacetaldehyde in a three-stage process, this compound is subjected to a condensation reaction with a malonic acid half-ester to give the piperonylidenecrotonic acid ester and this ester is converted into the corresponding piperidide by means of piperidine via three further stages (Chem. Ber. Volume 108 (1975), pages 95–108).

However, because of its many process steps and the unsatisfactory yields—the total yield is only 41%—this process is uneconomical and therefore cannot be used for preparing piperine on an industrial scale.

Piperine has also been prepared by condensation of piperonylideneacetaldehyde with piperidinocarbonylmethyltriphenylphosphonium iodide (Pharm. Chem. J. Volume 5 (1971), pages 462 to 464). However, this preparation has the disadvantage that the compounds to be employed as the reactants must in turn first be prepared by multi-stage processes, and that large amounts of triphenylphosphine oxide are formed during the condensation and can be separated off from the piperine only with difficulty. This process is therefore also unsuitable for synthesising piperine on an industrial scale.

It has now been found that known and new piperonylidenecrotonic acid amides of the formula

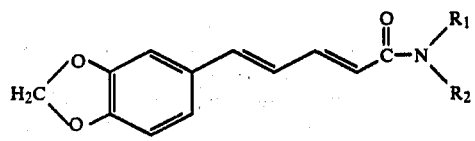

in which
R₁ and R₂ independently of one another represent hydrogen or an optionally substituted aliphatic, araliphatic or aromatic hydrocarbon radical, or, together with the nitrogen atom, form a heterocyclic ring, with the proviso that R₁ and R₂ do not simultaneously denote hydrogen, can be prepared in excellent yields in a simple manner when piperonal is reacted with crotonic acid amides of the formula

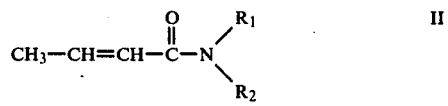

in which
R₁ and R₂ have the meaning indicated above, in the presence of hydroxides of the formula

in which
A⁺ represents a quaternary ammonium or phosphonium group or an alkali metal complex with neutral organic complex ligands, and polar aprotic or polar, sterically hindered protic solvents which are inert under the reaction conditions.

Compared with the processes known from the state of the art, the process according to the invention is distinguished by a considerably simplified procedure (few reaction stages and the use of condensation agents which can be handled industrially without special safety measures) and by substantially improved yields. Piperonylidenecrotonic acid amides can be prepared on an industrial scale without difficulty by the process according to the invention. The compounds are obtained in high purity.

It was in fact already known to subject aldehydes to condensation reactions with 3-methylbutenecarboxylic acid esters, 3-methylbutenecarboxylic acid amides or crotonic acid esters (U.S. Pat. No. 2,951,853; and Chem. Ber. Volume 106 (1973), pages 2,643–2,647). However, the condensation reactions were carried out using at least equimolar amounts, relative to the amount of alkenoic acid ester, of powerful condensation agents such as alkali metals, alkali metal amides, alkali metal hydrides or organometallic compounds, such as phenylsodium or triphenylmethylpotassium, and with complete exclusion of water.

It was therefore surprising that the reaction according to the invention already proceeds in high yields, even without exclusion of water, with catalytic amounts of condensation agents which are known to have a weaker action, such as ammonium or phosphonium hydroxides or hydroxides of alkali metal complexes with neutral organic complex ligands. In view of the fact that the reactivity of piperonal is comparable to that of 4-methoxybenzaldehyde, and since it was known that deactivated aldehydes such as 4-methoxybenzaldehyde react with crotonic acid ethyl ester to give the desired condensation product in only 12% yield, even in the presence of powerful condensation agents such as sodium amide (Chem. Ber. Volume 106 (1973), pages 2,643–2,647), it was to be expected that no reaction at all would take place under the reaction conditions according to the invention.

Furthermore, it was known that piperonal undergoes condensation with ethylidenemalonic acid esters in the presence of potassium hydroxide and ethanol or in the presence of a large excess of benzyltrimethylammonium hydroxide and methanol (J. Am. Chem. Soc. Volume 74

(1952), pages 5,527–5,529). However, if in this reaction the ethylidenemalonic acid ester, which is known to be very reactive, is replaced by crotonic acid amides, which are considerably slower to react, the yields of condensation product decrease to such an extent (down to about 10–15% of theory) that this reaction is of no interest for the preparation of piperonylidenecrotonic acid amides.

The quaternary ammonium and phosphonium hydroxides to be used according to the invention are compounds of the formula

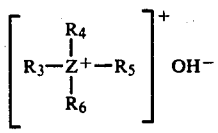

in which
Z represents phosphorus or, preferably, nitrogen and $R_3$, $R_4$, $R_5$ and $R_6$ independently of one another denote optionally substituted alkyl, cycloalkyl, aralkyl or aryl, two adjacent radicals $R_3$, $R_4$, $R_5$ and $R_6$, together with the central atom Z and optionally further hetero-atoms, form a heterocyclic ring or, in the case where Z denotes phosphorus, up to three of the radicals $R_3$, $R_4$, $R_5$ and $R_6$ represent a dialkylamino group.

For $R_3$, $R_4$, $R_5$ and $R_6$, examples of alkyl radicals which may be mentioned are, above all, $C_1$–$C_{18}$-alkyl radicals, such as the methyl, ethyl, propyl, sec.-butyl, heptyl, hexyl, i-octyl, dodecyl and octadecyl radical; examples of cycloalkyl radicals which may be mentioned are cyclopentyl radicals and, in particular, cyclohexyl radicals, which are optionally substituted by $C_1$–$C_4$-alkyl radicals; examples of aralkyl radicals which may be mentioned are benzyl radicals which are optionally substituted by $C_1$–$C_4$-alkyl radicals, methoxy groups or halogen; and an example of an aryl radical which may be mentioned is, above all, phenyl radicals substituted by $C_1$–$C_4$-alkyl groups, $C_1$–$C_2$-alkoxy groups or halogen atoms.

Examples which may be mentioned of heterocyclic rings which two adjacent radicals $R_3$, $R_4$, $R_5$ and $R_6$ can form, together with the central atom Z and optionally further hetero-atoms, such as oxygen, sulphur or nitrogen, are, above all, 5-membered or 6-membered heterocyclic rings, such as the pyrrolidine, piperidine or morpholine ring.

The dimethylamino group may be mentioned, above all, as a dialkylamino group.

Examples which may be mentioned of representatives of the ammonium and phosphonium hydroxides to be used according to the invention are: octylbenzyldimethylammonium hydroxide, octadecylbenzyldimethylammonium hydroxide, trimethylphenylphosphonium hydroxide, benzyltriethylammonium hydroxide, benzyltributylammonium hydroxide, benzyltrimethylammonium hydroxide, cetyltrimethylammonium hydroxide, methyltributylammonium hydroxide, tetradecyltrimethylammonium hydroxide, phenyltrimethylammonium hydroxide, tetrabutylammonium hydroxide, tetraethylammonium hydroxide, tetramethylammonium hydroxide, benzyldodecyldimethylammonium hydroxide, dimethylphenylbenzylammonium hydroxide, methyltrioctylammonium hydroxide, tetramethylphosphonium hydroxide, tetraethylphosphonium hydroxide, tetrabutylphosphonium hydroxide, tripropylbutylphosphonium hydroxide, benzyltrimethylphosphonium hydroxide, tris-(dimethylamino)-methylphosphonium hydroxide, tributylmethylphosphonium hydroxide, β-hydroxyethyltrimethylammonium hydroxide and β-hydroxyethyltriethylammonium hydroxide.

The compounds are known or can be prepared from the corresponding salts by known processes (see, for example, Houben-Weyl, Methoden der Organischen Chemie (Methods of Organic Chemistry), 4th edition, Volume 12/1, (1963), page 106).

The alkali metal complexes to be used according to the invention are alkali metal complexes of the neutral organic complex ligands known under the trival names "crown ethers", "cryptands" and "podands". The compounds are known as such or can be prepared by known methods (see, for example, U.S. Pat. Nos. 3,562,295, 3,860,611 and 3,966,766).

In general, cyclic polyethers containing a medium to large number of members, in which oxygen donor atoms are usually bonded by ethano bridges and which can contain one or more fused-on benzene or cyclohexane rings are designated "crown ethers" (see J. Am. Chem. Soc. 89, 7017 (1967); Chem. Rev. 74, 351 (1974) and Chem. Commun. 1976, 295).

In general, three-dimensional di-, tri- and tetracyclic aminopolyethers which contain a medium to large number of members are designated "cryptands" (see Endeavour 1971, 142 and J. Chem. Soc. 97, 6700 (1975)).

The "podands" are neutral ligands which are related to crown ethers but are not cyclic (see Tetrahedron Let. 1975, 2415).

Possible alkali metal ions for the alkali metal complexes are lithium ions and, in particular, potassium and sodium ions.

Examples which may be mentioned of representatives of the alkali metal complexes with crown ethers, cryptands and podands to be used according to the invention are: the potassium complexes with 1,4,7,10,13,16-hexaoxacyclooctadecane (18-crown-6), 1,13-bis-(8-quinolyl)-1,4,7,10,13-pentaoxatridecane, 4,7,13,16,21,24-hexaoxa-1,10-diazabicyclo[8,8,8]-hexacosane, 5,6-benzo-4,7,13,16,21,24-hexaoxa-1,10-diazabicyclo[8,8,8]-hexacosane, 5,6,14,15-dibenzo-4,7,13,16,21,24-hexaoxa-1,10-diazabicyclo[8,8,8]-hexacosane, 5-decyl-4,7,13,16,21,24-hexaoxa-1,10-diazabicyclo[8,8,8]-hexacosane, 1,4,7,14,23-pentaoxa[7,2]-orthocyclo[2](2,6)-pyridinophane (dibenzopyridino-18-crown-6), 1,4,7,14,17,20-hexaoxa[7,7]orthocyclophane (dibenzo-18-crown-6) and 2,5,8,15,18,21-hexaoxatricyclo[20,4,0,0$^{9,14}$]hexacosane (dicyclohexyl-18-crown-6); the sodium complexes with 1,4,7,10,13-pentaoxacyclopentadecane (15-crown-5) and 4,7,13,16,21-pentaoxa-1,10-diazabicyclo[8,5,5]tricosane; and the lithium complexes with 1,4,7,10-tetraoxacyclododecane (12-crown-4) and 4,7,13,18-tetraoxa-1,10-diazabicyclo[8,5,5]eicosane The hydroxides of the formula III to be used according to the invention can be employed as such, that is to say in the isolated form. However, they can also be produced only in the reaction mixture, for example by adding appropriate amounts of sodium hydroxide or potassium hydroxide to the ammonium or phosphonium salts or to the neutral organic complex ligands.

In general, the hydroxides of the formula III are used in amounts of 0.04–0.2 mol, preferably 0.05–0.1 mol, per mol of piperonal.

Examples which may be mentioned of polar aprotic solvents which are inert under the reaction conditions are: relatively weakly polar aprotic solvents, such as aromatic hydrocarbons, for example toluene or xylene, but in particular the more strongly polar aprotic solvents, such as aliphatic, araliphatic or cyclic ethers, for example dibutyl ether, ethylene glycol dimethyl ether, diethylene glycol dimethyl ether, diethylene glycol diethyl ether, anisole, tetrahydrofurane and dioxane; acid amides, for example dialkylformamides or dialkylacetamides, such as dimethylformamide or dimethylacetamide, or N-methyl-2-pyrrolidinone; tetraalkylureas, such as tetramethylurea; sulphoxides, for example dialkylsulphoxides, such as dimethylsulphoxide, and tetrahydrothiophene 1-oxide; sulphones, such as tetrahydrothiophene 1,1-dioxide; hexaalkylphosphoric acid diamides, such as hexamethylphosphoric acid triamide, or 1-methyl-1-oxophospholine; and tertiary amines, such as tributylamine, dimethylaniline or dimethylbenzylamine.

Polar, sterically hindered protic solvents which may be mentioned are, above all, tertiary butanol and 1,1-dimethylhexanol.

The amounts in which the abovementioned organic solvents are employed can vary within wide limits; in general, it has proved suitable to employ 50–500, preferably 100–350, ml of solvent per mol of piperonal.

It is possible to increase the amount of solvent above the maximum amount mentioned of 500 ml, but in general this is of no advantage.

In general, the condensation according to the invention is carried out at temperatures between 20° C. and 100° C., preferably between 50° C. and 80° C.

The reaction can be carried out under normal pressure or increased pressure. In general, it is carried out under normal pressure. It is preferably carried out in an inter gas atmosphere, for example under nitrogen or argon.

In general, the two reactants are employed in the process according to the invention in approximately equimolar amounts; it has proved suitable to use 1 to 1.2 mols of crotonic acid amide, preferably 1 to 1.1 mols of crotonic acid amide, per mol of piperonal.

The piperonylidenecrotonic acid amides prepared according to the invention are isolated from the reaction mixture by evaporating off the solvent and are freed from soluble impurities, for example, by washing with water. The compounds can be purified by recrystallisation.

The course of the process according to the invention may be illustrated by the equation which follows:

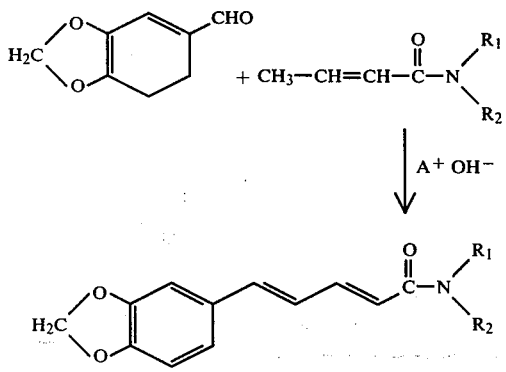

For $R_1$ and $R_2$, examples of optionally substituted aliphatic hydrocarbon radicals which may be mentioned are, above all, $C_1$–$C_6$-alkyl radicals, $C_1$–$C_6$-alkenyl radicals and 5-membered and 6-membered cycloalkyl radicals, for example the methyl, ethyl, n-propyl, i-propyl, n-butyl, sec.-butyl, i-pentyl, n-hexyl, i-hexyl, allyl, cyclopentyl and cyclohexyl radical, and furthermore cyclopentyl and cyclohexyl radicals substituted by $C_1$–$C_4$-alkyl groups, such as the 4-methyl- and 2,4-dimethyl-cyclohexyl radical, possible substituents of the alkyl radicals being, above all, halogen atoms, such as the chlorine atom, and the hydroxyl group and examples of substituted alkyl radicals being the 2-chloroethyl and 2-hydroxyethyl radical; examples which may be mentioned of optionally substituted araliphatic and aromatic hydrocarbon radicals are, above all, the benzyl and phenyl radical and benzyl and phenyl radicals which are substituted by halogen atoms, for example chlorine or bromine atoms, or by $C_1$–$C_4$-alkyl groups and $C_1$–$C_4$-alkoxy groups, such as the 4-methyl-and 3-chloro-benzyl radical and the 3-chloro, 2,4-dichloro-, 2-bromo-4-methyl, 4-ethyl- and 4-methoxy-phenyl radical; and examples which may be mentioned of heterocyclic rings which $R_1$ and $R_2$ can form, together with the amide nitrogen, are, above all, 5-membered to 7-membered heterocyclic rings optionally containing further hetero-atoms, such as oxygen, sulphur or nitrogen, such as the piperidine, pyrrolidine, morpholine and hexamethyleneimine ring, it also being possible for these heterocyclic rings to be substituted, for example by $C_1$–$C_4$-alkyl groups, examples being 2-, 3-and 4-methylpiperidine, 2,3-, 2,4- and 2,6-dimethylpiperidine, 2-ethyl-piperidine and 2,4,6-trimethylpiperidine.

The crotonic acid amides to be used, according to the invention, as starting compounds are known or can be prepared by processes which are in themselves known, for example from crotonoyl chloride and the corresponding amines (Helv. Chim. Acta Volume 38 (1955), pages 1,085–1,095) or from the corresponding ammonium salts of crotonic acid, either by splitting off water at elevated temperature, optionally in the presence of acid catalysts, or by reaction with inorganic acid halides, for example thionyl chloride (Houben-Weyl, Methoden der organischen Chemie (Methods of Organic Chemistry), Volume XI/2, pages 3–9, Thieme Verlag Stuttgard 1958).

Examples which may be mentioned of representatives of the crotonic acid amides to be reacted according to the invention are: crotonic acid piperidide, crotonic acid pyrrolidide, crotonic acid morpholide, crotonic acid hexamethyleneimide, crotonic acid 2-methyl-piperidide, crotonic acid 3-methylpiperidide, crotonic acid 4-methylpiperidide, crotonic acid 2-pentylpiperidide, crotonic acid 4-pentylpiperidide, crotonic acid 2,4,6-trimethylpiperidide, crotonic acid 2,6-dimethyl-piperidide, crotonic acid 2,4-dimethylpiperidide, crotonic acid crotonic acid 2-ethylpiperidide, crotonic acid 2,3-dimethylpiperidide, crotonic acid methylamide, crotonic acid ethylamide, crotonic acid propylamide, crotonic acid allylamide, crotonic acid butylamide, crotonic acid isobutylamie, crotonic acid isopentylamide, crotonic acid cyclohexylamide, crotonic acid 3-ethyl-heptylamide, crotonic acid benzylamide, crotonic acid 3,4-methylenedioxy-anilide, crotonic acid anilide, crotonic acid 2-bromo-4-methyl-anilide, crotonic acid dimethylamide, crotonic acid diethylamide, crotonic acid dipropylamide, crotonic acid diisopropylamide, crotonic acid diallylamide, crotonic acid dibutylamide, crotonic acid diisobutylamide, crotonic acid dicyclohexylamide, crotonic acid di-β-chloroethyl-amide and crotonic acid di-β-hydroxyethyl-amide.

Examples which may be mentioned of representatives of the piperonylidenecrotonic acid amides which can be prepared by the process according to the invention are: piperonylidenecrotonic acid piperidide, piperonylidenecrotonic acid pyrrolidide, piperonylidenecrotonic acid morpholide, piperonylidenecrotonic acid hexamethyleneimide, piperonylidenecrotonic acid 2-methylpiperidide, piperonylidenecrotonic acid 3-methylpiperidide, piperonylidenecrotonic acid 4-methylpiperidide, piperonylidenecrotonic acid 2-pentylpiperidide, piperonylidenecrotonic acid 4-pentylpiperidide, piperonylidenecrotonic acid 2,4,6-trimethylpiperidide, piperonylidenecrotonic acid 2,6-dimethylpiperidide, piperonylidenecrotonic acid 2,4-dimethylpiperidide, piperonylidenecrotonic acid 2-ethylpiperidide, piperonylidenecrotonic acid 2,3-dimethylpiperidide, piperonylidenecrotonic acid methylamide, piperonylidenecrotonic acid ethylamide, piperonylidenecrotonic acid propylamide, piperonylidenecrotonic acid allylamide, piperonylidenecrotonic acid butylamide, piperonylidenecrotonic acid isobutylamide, piperonylidenecrotonic acid isopentylamide, piperonylidenecrotonic acid cyclohexylamide, piperonylidenecrotonic acid 3-ethyl-heptylamide, piperonylidenecrotonic acid benzylamide, piperonylidenecrotonic acid 3,4-methylenedioxy-anilide, piperonylidenecrotonic acid anilide, piperonylidenecrotonic acid 2-bromo-4-methyl-anilide, piperonylidenecrotonic acid dimethylamide, piperonylidenecrotonic acid diethylamide, piperonylidenecrotonic acid dipropylamide, piperonylidenecrotonic acid diisopropylamide, piperonylidenecrotonic acid diallylamide, piperonylidenecrotonic acid dibutylamide, piperonylidenecrotonic acid diisobutylamide, piperonylidenecrotonic acid dicyclohexylamide, piperonylidenecrotonic acid di-β-chloroethyl-amide and piperonylidenecrotonic acid di-β-hydroxyethyl-amide.

The parts indicated in the examples which follow are parts by weight, unless it has been indicated otherwise.

EXAMPLE 1

23 parts of triethylbenzylammonium chloride and 10 parts of 50% strength aqueous potassium hydroxide solution are added to a solution of 150 parts (1 mol) of piperonal and 170 parts (1.1 mols) of crotonic acid piperidide in 100 parts by volume of dimethylsulphoxide at 25° C. under nitrogen. The reaction mixture is stirred at 25° C. for 15 minutes and then at 60° to 65° C. for 2 hours, and thereafter is freed from solvent in vacuo. 400 parts by volume of water are added to the residue. The reaction product which has precipitated is filtered off, washed with water and dried. Yield: 276 parts of crude piperonylidenecrotonic acid piperidide.

After recrystallisation from ethyl acetate, the yield of pure piperonylidenecrotonic acid piperidide is 251 parts (= 88% of theory). Melting point 129°–130° C.

EXAMPLES 2–7

1 mol of piperonal is reacted with 1.1 mols of a crotonic acid amide, indicated in Table 1 below, in the presence of 0.09 mol of triethylbenzylammonium hydroxide under the conditions indicated in Example 1. The piperonylidenecrotonic acid amides listed in Table 1 are obtained in the yields likewise indicated in the table.

Table 1

Formulae of the crotonic acid amides (a) employed and the piperonylidenecrotonic acid amides (b) obtained therefrom

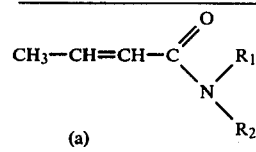
(a)

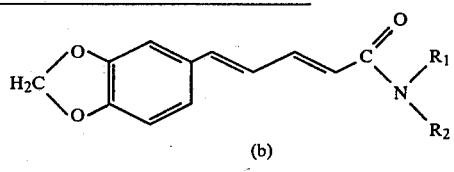
(b)

| Example No. | N R₁ / R₂ | Yield in % of theory | Melting point in °C. |
|---|---|---|---|
| 2 | (piperidine ring) | 83 | 142–143 |
| 3 | (morpholine ring) | 81 | 167–168 |
| 4 | HN—CH₂—CH(CH₃)₂ | 78 | 165–166 |
| 5 | N(C₂H₅)₂ | 84 | 94–95 |
| 6 | N(CH₂—CH=CH₂)₂ | 86 | 75–76 |
| 7 | HN—(phenyl) | 80 | 197–198 |

EXAMPLES 8-14

1 mol of piperonal is reacted with 1.1 mols of crotonic acid piperidide in the presence of 0.09 mol of a hydroxide, indicated in Table 2 below, under the reaction conditions described in Example 1 to give piperonylidenecrotonic acid piperidide. The yields obtained are likewise indicated in Table 2.

Table 2

| Example No. | Formula of the hydroxides employed A⊕OH⊖ A⊕ | Yield in % of theory |
|---|---|---|
| 8 | (CH₃)₃N—⟨phenyl⟩ | 82 |
| 9 | (CH₃)₂N—(CH₂)₁₁—CH₃ \| CH₂—⟨phenyl⟩ | 74 |
| 10 | (CH₃)₃N—CH₂—⟨phenyl⟩ | 76 |
| 11 | (C₂H₅)₄N | 80 |
| 12 | (C₄H₉)₄N | 78 |
| 13 | (C₈H₁₇)₃N—CH₃ | 73 |
| 14 | 18-crown-6 K complex | 86 |

EXAMPLES 15-23

1 mol of piperonal is reacted with 1.1 mols of crotonic acid piperidide in the presence of 0.09 mol of triethylbenzylammonium hydroxide in 100 parts by volume of one of the solvents indicated in Table 3 which follows, under the conditions described in Example 1 to give piperonylidenecrotonic acid piperidide. The yields achieved are likewise indicated in Table 3.

Table 3

| Example No. | Solvent | Yield in % of theory |
|---|---|---|
| 15 | dimethoxyethane | 75 |
| 16 | diethylene glycol dimethyl ether | 81 |
| 17 | tert.-butanol | 69 |
| 18 | tetrahydrothiophene 1,1-dioxide | 71 |
| 19 | N-methylpyrrolidinone | 72 |
| 20 | tetrahydrofurane | 68 |
| 21 | dimethylbenzylamine | 76 |
| 22 | dimethylacetamide | 73 |
| 23 | anisole | 80 |

EXAMPLE 24

First 2.6 parts of 18-crown-6 and then one part of 50% strength aqueous potassium hydroxide solution are added to a solution of 15 parts (0.1 mol) of piperonal and 17 parts (0.11 mol) of crotonic acid piperidide in 10 parts by volume of toluene at 25° C. under nitrogen. The reaction mixture is stirred at 25° C. for 15 minutes and then at 60 to 65° C. for 2 hours, and is subsequently freed from the solvent in vacuo. 40 parts by volume of water are added to the residue. The reaction product which has precipitated is filtered off, washed with water and dried. Yield: 24 parts of crude piperonylidenecrotonic acid piperidide.

After recrystallisation from ethyl acetate, the yield of pure piperonylidenecrotonic acid piperidide is 19.2 parts (= 67% of theory). Melting point 129°-130° C.

EXAMPLE 25

First 2.3 parts of triethylbenzylammonium chloride and then one part by weight of 40% strength aqueous sodium hydroxide solution are added to a solution of 15 parts (0.1 mol) of piperonal and 17 parts (0.11 mol) of crotonic acid piperidide in 10 parts by volume of dimethylsulphoxide at 25° C. under nitrogen. The reaction mixture is stirred at 25° for 15 minutes and then at 60° to 65° C. for 2 hours, and is subsequently freed from the solvent in vacuo. The residue is stirred with 40 parts by volume of water. The reaction product which has precipitated is filtered off, washed with water and dried. Yield of crude piperonylidencrotonic acid piperidide: 27 parts.

After recrystallisation from ethyl acetate, the yield of pure piperonylidenecrotonic acid piperidide is 23 parts (= 80% of theory). Melting point: 129°-130° C.

EXAMPLE 26

4 parts of a 40% strength aqueous solution of benzyltrimethylammonium hydroxide are added to a solution of 15 parts (0.1 mol) of piperonal and 17 parts (0.11 mol) of crotonic acid piperidide in 10 parts by volume of anisole at 25° C. under nitrogen. The reaction mixture is stirred at 60° to 65° C. for 2 hours and is then freed from the solvent in vacuo. The residue is stirred with 40 parts by volume of water. The reaction product obtained in filtered off, washed with water and dried. Yield of crude piperonylidenecrotonic acid piperidide: 27 parts.

After recrystallisation from ethyl acetate, the yield of pure piperonylidenecrotonic acid piperidide is 22.5 parts (= 79%). Melting point: 129°-130° C.

EXAMPLE 27

10 parts by weight of a 50% strength potassium hydroxide solution are added to a solution of 150 parts (1 mol) of piperonal, 170 parts (1.1 mols) of crotonic acid piperidide and 25 g of benzyldimethylphenylammonium chloride in 100 parts by volume of anisole at 25° C. under nitrogen. The reaction mixture is stirred at 25° C. for 15 minutes and then at 60°-65° C. for 2 hours, and is subsequently freed from the solvent in vacuo.

The residue is stirred with 400 parts by volume of water. The reaction product obtained is filtered off, washed with water and dried. Yield of crude piperonylidenecrotonic acid piperidide: 279 parts.

After recrystallisation from ethyl acetate, the yield of pure piperonylidenecrotonic acid piperidide is 251 parts (= 88% of theory). Melting point: 129°-130° C.

EXAMPLE 28

The procedure followed is as in Example 28, but the benzyldimethylphenylammonium chloride employed in that example is replaced by 34 parts by weight of benzyldodecyldimethylammonium chloride. Yield of pure piperonylidenecrotonic acid piperidide: 245 parts (= 85% of theory). Melting point: 129°–130° C.

What is claimed is:

1. A process for the preparation of a piperonylidenecrotonic acid amide of the formula

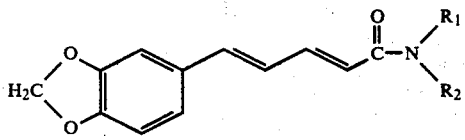

in which

R₁ and R₂ independently of one another represent hydrogen or an optionally substituted aliphatic, araliphatic or aromatic hydrocarbon radical, or, together with the nitrogen atom, form a heterocyclic ring, with the proviso that R₁ and R₂ do not simultaneously denote hydrogen, comprising reacting piperonal with a crotonic acid amide of the formula

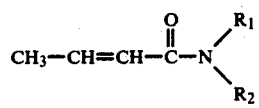

in which

R₁ and R₂ have the meaning indicated above, in the presence of a hydroxide of the formula

A⁺ OH⁻ in which

A⁺ represents a quaternary ammonium or phosphonium group or an alkali metal complex of a crown ether, podand or crytand, and a polar aprotic or polar, sterically hindered protic organic solvent which is inert under the reaction conditions.

2. A process according to claim 1, wherein the hydroxide is an ammonium or phosphonium salt of the formula

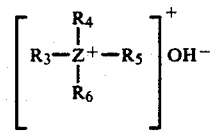

in which

Z represents phosphorus or, preferably, nitrogen and R₃, R₄, R₅ and R₆ independently of one another denote optionally substituted alkyl, cycloalkyl, aralkyl or aryl, two adjacent radicals R₃, R₄, R₅ and R₆, together with the central atom Z and optionally further hetero-atoms, form a heterocyclic ring or, in the case where Z denotes phosphorus, up to three of the radicals R₃, R₄, R₅ and R₆ represent a dialkylamino group.

3. A process according to claim 1, wherein the hydroxide is an alkali metal complex of a crown ether, a podand or a cryptand.

4. A process according to claim 1, wherein the inert polar aprotic solvent is a relatively strongly polar aprotic organic solvent.

5. A process according to claim 1, wherein the inert polar aprotic solvent is an aliphatic, araliphatic or cylic ether, an acid amide, a sulphoxide, a sulphone, a hexaalkylphosphoric acid diamide or a tertiary amine.

6. A process according to claim 1, wherein the hydroxide is employed in an amount of 0.04 –0.2 mol per mol or piperonal.

* * * * *

UNITED STATES PATENT AND TRADEMARK OFFICE
CERTIFICATE OF CORRECTION

PATENT NO. : 4,209,445
DATED : June 24, 1980
INVENTOR(S) : HERMANN OEDIGER and ANDREAS SCHULZE It is certified that error appears in the above—identified patent and that said Letters Patent is hereby corrected as shown below:

| Column | Line | |
|---|---|---|
| Line 2 of the Abstract: | | "acids" should be --acid--. |
| 3 | 68 | delete "k". |
| 4 | 14 | "trival" should be --trivial--. |
| 6 | 46 | "Stuttgard" should be --Stuttgart--. |
| 6 | 61 | "isobutylamie" should be --isobutylamide--. |
| 10 | 40 | "in" should be --is--. |
| 12 | 37 | "or" should be --of--. |

Signed and Sealed this

Seventh Day of October 1980

[SEAL]

Attest:

SIDNEY A. DIAMOND

Attesting Officer

Commissioner of Patents and Trademark

UNITED STATES PATENT AND TRADEMARK OFFICE
CERTIFICATE OF CORRECTION

PATENT NO. : 4,209,445       Page 1 of 2
DATED      : June 24, 1980
INVENTOR(S): Hermann Oediger and Andreas Schulze It is certified that error appears in the above—identified patent and that said Letters Patent is hereby corrected as shown below:

| Column | Line | |
|---|---|---|
| 5 | 37 | Change "inter" to --inert--. |
| 5 | 55 | In that portion of the equation which reads: |

"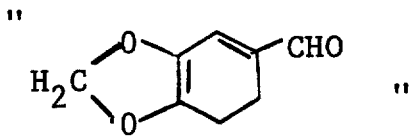"

insert the missing bond line as follows:

--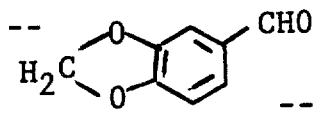--

(This is at the upper lefthand portion of the equation)

| | | |
|---|---|---|
| 6 | 56 | delete "cro-" |
| 6 | 57 | delete "tonic acid" |

UNITED STATES PATENT AND TRADEMARK OFFICE
CERTIFICATE OF CORRECTION

PATENT NO. : 4,209,445
DATED : June 24, 1980
INVENTOR(S) : Hermann Oediger and Andreas Schulze It is certified that error appears in the above—identified patent and that said Letters Patent is hereby corrected as shown below:

| Column | Line | |
|---|---|---|
| 9 | 33 | change "c" in the diagram to --o-- |

Signed and Sealed this

Seventeenth Day of February 1981

[SEAL]

Attest:

RENE D. TEGTMEYER

Attesting Officer     Acting Commissioner of Patents and Trademarks